United States Patent [19]

Imazio

[11] Patent Number: Plant 5,430

[45] Date of Patent: Apr. 9, 1985

[54] HEATHER NAMED ERICA PACIFICA

[75] Inventor: Bruno L. Imazio, Watsonville, Calif.

[73] Assignee: Bruno Imazio Partnership, Watsonville, Calif.

[21] Appl. No.: 478,740

[22] Filed: Mar. 25, 1983

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Charles W. Rummler

[57] ABSTRACT

A new variety of heather particularly characterized by a very early blooming habit and a profuse production of light pink lavender flowers which appear in rapid uninterrupted succession from the base of the stem to its tip end.

2 Drawing Figures

BACKGROUND OF THE NEW PLANT

My new variety of heath was discovered by me in 1978 as a seedling of unknown pollen parentage growing in a cultivated field of *Erica regerminans.* The very extraordinary growth and blooming habit of the new plant prompted me to isolate the plant and reproduce it by cuttings, and continuous work with cutting propagation of the plant during the five years since its discovery has now resulted in a field of blooming plants of sufficient size to assure that the new variety will hold its novel characteristics. The new plant has a more delicate color than the deeper lavender color of regerminans, it forms and developes its blooms at a faster rate, and it developes its full bloom substantially a month advance of its parent regerminans. This variety is now being grown for the commercial market at Watsonville, Calif.

DESCRIPTION OF THE DRAWINGS

My new heather variety is illustrated by the accompanying photographic drawings, the upper view of which shows a closeup view of a stem of flowers of the new plant and the lower view shows a row of the new plants in full bloom alongside a stand of the parent *Erica regerminans* which is just beginning to come into bloom. The views of the new variety, which were photograhed during the second week of October 1982, show in a general way the overall appearance of this plant.

The following is a detailed description of the new plant based upon observations of field grown plants made during September and October 1982, the colors specified being as close as could reasonably be determined from the very small flowers of this plant.

THE PLANT

Origin: Seedling.

Parentage:

*Speed parent.*—*Erica regerminans.*

*Pollen parent.*—Unknown.

Classification:

*Botanic.*—*Erica regerminans* Pacifica.

Commercial.—Pacifica heather.

Form: Woody shrub.

Shape: Generally upright, stems curving slightly to accommodate fullness of the plant.

Height: About 2 feet.

Main stem length: About 20" when full grown.

Branching: Generous. This plant is pruned yearly to encourage branching and fullness.

Growth: Vigorous with medium strength.

Foliage: Abundant with tiny needle-like leaves over the entire plant.

*Size of leaf.*—$\frac{1}{8}$ To $\frac{1}{4}$ inch long.

*Shape of leaf.*—Long and very narrow.

*Color.*—Dark green.

*Texture.*—Fuzzy.

In general, the foliage is too tiny to determine further characteristics by on plant observation.

THE BUD

Size:

*Length.*—$\frac{1}{8}$" And less.

*Diameter.*—Very small.

Shape: Tear drop with rounded base resting in calyx.

Rate of opening: Progressive and continuous beginning at base of stem and progressing rapidly to tip of stem.

Petals: The bud has no petals or sepals.

Color: The buds are too tiny for accurate determination.

INFLORESCENCE

Blooming habit: Annually, once in early fall.

Size of bloom: Miniscule; less than $\frac{1}{8}$ inch in diameter and depth.

Shape of flower: Bell-shaped.

Appearance: Satiny.

Color: Pale Pinkish Lavender, R.H.S. 62C, in overall appearance of plant.

Flower stem:

*Length.*—About $\frac{1}{4}$ inch to 6 inches.

*Color.*—Light Brown.

*Strength.*—Woody and supple.

*Branching.*—Upright and about 45° from main stem.

Discoloration: Slight deepening of color after full bloom.

Effect of weather: Prolonged exposure to hot or wet weather is detrimental to plant appearance.

Persistence: Blooms persist long after plant ceases to draw water. Blooms do not shed easily.

Fragrance: Mildly wild.

Lasting quality:

*On plant.*—2 Months.

*As cut flower.*—4 Weeks.

This new variety of heather originated as a seedling found among a field of regerminans and is reproduced only by cuttings. The new variety differs visually in the following respects:

The color of the new plant is a more delicate pale pinkish lavender whereas the parent is of a deeper color and more lavender.

The foliage of the new plant is more dense than the parent and its leaves are finer and smaller.

The branches of the main stem of the new plant are more elongated than those of the parent.

The blooms of the new plant do not readily shed after passing their peak. The flowers of the parent shed readily.

The outstanding characteristic of the new plant is that it is in full bloom to the tip of its stem a full month before the parent variety, whereas the parent variety is just beginning to flower at its base and at the peak of its season still has green tips with no bloom. This early blooming habit is an important feature of the new variety, since heather is a plant that cannot be manipulated to bloom as may be desired. It has its season and that is invariable and often, simply to meet the fall season demand, the parent variety has to be harvested prematurely. This new heather cures this problem.

I claim:

1. A new variety of heather, substantially as herein shown and described, particularly characterized by its very early blooming habit as compared with its seed parent.

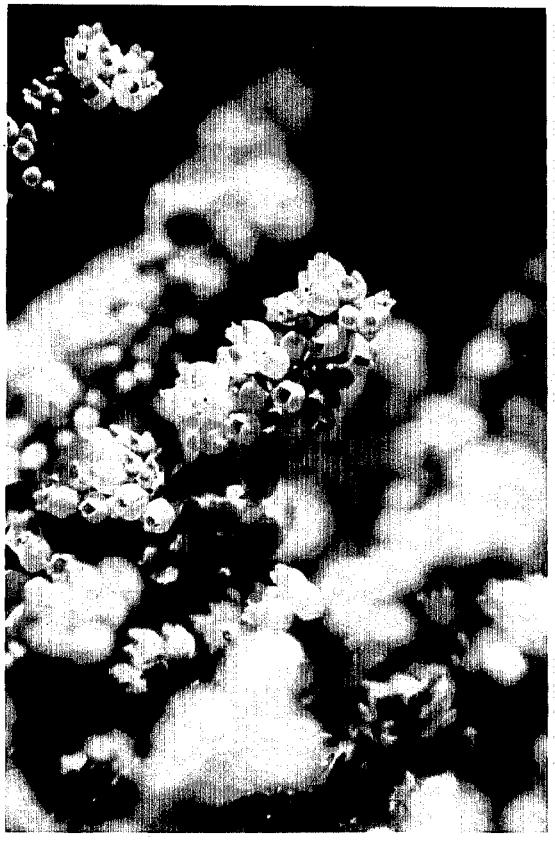
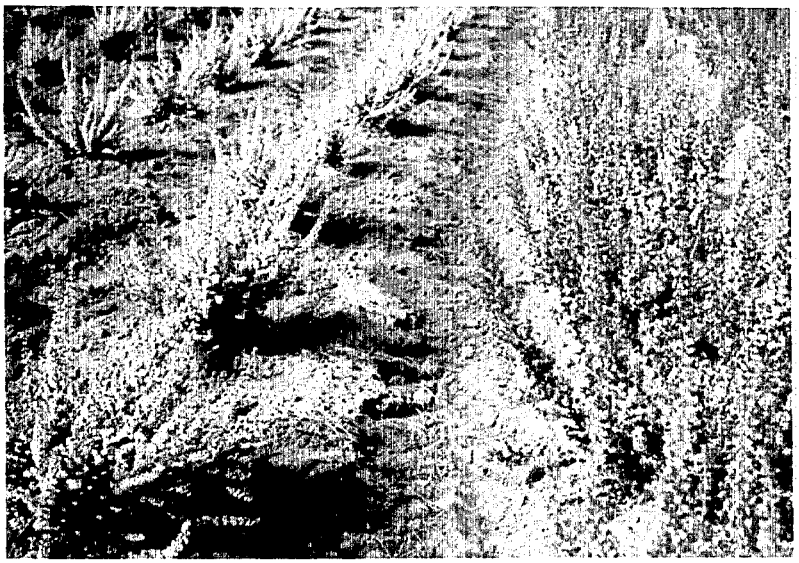

* * * * *